US00PP31736P2

(12) United States Plant Patent
Murray

(10) Patent No.: US PP31,736 P2
(45) Date of Patent: May 5, 2020

(54) ***LOMANDRA* PLANT NAMED 'SPRILOMJAN'**

(50) Latin Name: ***Lomandra confertifolia* ssp. *pallida***
Varietal Denomination: Sprilomjan

(71) Applicant: Joseph Murray, Officer (AU)

(72) Inventor: Joseph Murray, Officer (AU)

( * ) Notice: Subject to any disclaimer, the term of this patent is extended or adjusted under 35 U.S.C. 154(b) by 0 days.

(21) Appl. No.: 16/501,608

(22) Filed: May 7, 2019

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
CPC ..... A01H 5/00; A01H 6/12
See application file for complete search history.

*Primary Examiner* — Annette H Para
(74) *Attorney, Agent, or Firm* — C. A. Whealy

(57) ABSTRACT

A new and distinct cultivar of *Lomandra* plant named 'Sprilomjan', characterized by its upright plant habit with foliage initially erect to slightly outwardly leaning; vigorous growth habit during propagation and subsequent nursery production; numerous leaves, dense and bushy appearance; long narrowly lanceolate leaves that are yellow green in color; and good garden performance.

2 Drawing Sheets

Botanical designation: *Lomandra confertifolia* ssp. *pallida.*

Cultivar denomination: 'SPRILOMJAN'.

BACKGROUND OF THE INVENTION

The present invention relates to a new and distinct cultivar of *Lomandra* plant, botanically known as *Lomandra confertifolia* ssp. *pallida*, and hereinafter referred to by the name 'Sprilomjan'.

The new *Lomandra* plant is a product of a planned breeding program conducted by the Inventor in Pakenham, Victoria, Australia. The objective of the breeding program is to create new upright *Lomandra* plants with strong plant growth in propagation and subsequent nursery production.

The new *Lomandra* plant originated from an open-pollination in Pakenham, Victoria, Australia in 2014, of an unidentified selection of *Lomandra confertifolia* ssp. *pallida*, not patented, as the female, or seed parent with an unknown selection of *Lomandra confertifolia* ssp. *pallida* as the male, or pollen, parent. The new *Lomandra* plant was discovered and selected by the Inventor as a single plant from within the progeny of the stated open-pollination in a controlled environment in Pakenham, Victoria in 2016.

Asexual reproduction of the new *Lomandra* plant by in vitro micropropagated tip cuttings in Pakenham, Victoria, Australia since 2016 has shown that the unique features of this new *Lomandra* plant are stable and reproduced true to type in successive generations.

SUMMARY OF THE INVENTION

Plants of the new *Lomandra* have not been observed under all possible combinations of environmental conditions and various cultural practices. The phenotype may vary somewhat with variations in environmental conditions such as temperature and light intensity, without, however, any variance in genotype.

The following traits have been repeatedly observed and are determined to be the unique characteristics of 'Sprilomjan'. These characteristics in combination distinguish 'Sprilomjan' as a new and distinct *Lomandra* plant:

1. Upright plant habit with foliage initially erect to slightly outwardly leaning.
2. Vigorous growth habit during propagation and subsequent nursery production.
3. Numerous leaves, dense and bushy appearance.
4. Long narrowly lanceolate leaves that are yellow green in color.
5. Good garden performance.

Plants of the new *Lomandra* differ from plants of the female parent selection in the following characteristics:

1. Plants of the new *Lomandra* grow more vigorously during propagation than plants of the female parent selection.
2. Plants of the new *Lomandra* are denser than plants of the female parent selection.

Plants of the new *Lomandra* can be compared to plants of the *Lomandra hybrida* 'Lomlon', disclosed in U.S. Plant Pat. No. 23,034. In side-by-side comparisons, plants of the new *Lomandra* differ primarily from plants of the 'Lomlon' in the following characteristics:

1. Plants of the new *Lomandra* are more vigorous than plants of 'Lomlon'.
2. Plants of the new *Lomandra* are denser than plants of 'Lomlon'.
3. Plants of the new *Lomandra* have shorter inflorescences and peduncles than plants of 'Lomlon'.

BRIEF DESCRIPTION OF THE PHOTOGRAPHS

The accompanying photographs illustrate the overall appearance of the new *Lomandra* plant showing the colors as true as it is reasonably possible to obtain in colored reproductions of this type. Colors in the photographs may differ slightly from the color values cited in the detailed botanical description which accurately describe the colors ofthe new *Lomandra* plant.

The photograph on the first sheet comprises side perspective view of a typical plant of 'Sprilomjan' grown in a container.

The photograph on the second sheet is a close-up view of a typical flowering plant of 'Sprilomjan'.

DETAILED BOTANICAL DESCRIPTION

The aforementioned photographs and following observations and measurements describe plants grown during the summer and autumn in 30-cm containers in an outdoor nursery in Peats Ridge, New South Wales, Australia and under conditions and practices which approximate those generally used in commercial *Lomandra* plant production. During the production of the plants, day temperatures ranged from 23° C. to 28° C., night temperatures ranged from 10° C. to 18° C. and light levels ranged from 100 to 110 klux. Plants were two years old when the photographs and the botanical description were taken. In the following description, color references are made to The Royal Horticultural Society Colour Chart, 2015 Edition, except where general terms of ordinary dictionary significance are used.

Botanical classification: *Lomandra confertifolia* ssp. *pallida* 'Sprilomjan'.

Parentage:

*Female, or seed, parent.*—Unidentified selection of *Lomandra confertifolia* ssp. *pallida*, not patented.

*Male, or pollen, parent.*—Unknown selection of *Lomandra confertifolia* ssp. *pallida*, not patented.

Propagation:

*Type.*—By in vitro micropropagated cuttings.

*Time to initiate roots, summer.*—About seven to ten days at temperatures of about 20° C. to 25° C.

*Time to initiate roots, winter.*—About ten days to two weeks at temperatures of about 15° C. to 20° C.

*Time to produce a rooted young plant, summer.*—About 25 to 30 days at temperatures of about 20° C. to 25° C.

*Time to produce a rooted young plant, winter.*—About 35 to 40 days at temperatures of about 15° C. to 20° C.

*Root description.*—Medium thickness, fibrous; typically white in color, actual color of the roots is dependent on substrate composition, water quality, fertilizers, substrate temperature and age of roots.

*Rooting habit.*—Moderately freely branching, spreading; dense.

*Rhizome length.*—About 2 cm to 4 cm.

*Rhizome texture.*—Smooth, glabrous.

*Rhizome color.*—Close to 155C.

Plant description:

*Plant and growth habit.*—Upright plant habit with foliage initially erect to somewhat outwardly leaning; narrow inverted triangle; dense and bushy appearance with about 250 leaves per plant; vigorous growth habit.

*Plant height.*—About 100 cm.

*Plant diameter or spread.*—About 80 cm.

Leaf description:

*Orientation.*—Initially erect to outwardly leaning.

*Length.*—About 50 cm to 60 cm.

*Width.*—About 3 mm to 4 mm; broadening towards the base to about 5 mm.

*Shape.*—Narrowly lanceolate.

*Apex.*—Emarginate.

*Base.*—Cauline.

*Margin.*—Entire.

*Cross-sectional profile.*—Initially, flat in profile and with maturity, slightly concave.

*Texture and luster, upper and lower surfaces.*—Smooth, glabrous; slightly to moderately glossy.

*Venation pattern.*—Parallel.

*Color.*—Developing leaves, upper and lower surfaces: Close to 146A, not variegated. Fully expanded leaves, upper and lower surfaces: Close to 146A, not variegated; venation, close to 146A. Basal leaf sheath: Initially, close to 146A; with development, close to 166A and N167B to N167B.

Flower description:

*Flower arrangement and flowering habit.*—Sessile male flowers arranged in upright spikes; spikes displayed within the foliar plane on relatively short peduncles; flowers face mostly upright to outwardly.

*Fragrance.*—Faintly to moderately fragrant, pleasant.

*Flowering season.*—Plants begin flowering in the spring and continue to flower during the summer until the autumn in New South Wales, Australia.

*Flower longevity.*—Individual flowers last about ten days on the plant; flowers persistent.

*Spike length.*—About 7 cm to 8 cm.

*Spike diameter.*—About 3 cm to 3.5 cm.

*Flower buds.*—Ovoid in shape and close to 159C in color becoming closer to 154C to 154D with development.

*Floral bracts.*—Length: About 9 mm to 3.8 cm. Color: Close to 159C and 11A to 11C.

*Peduncles* (*spike stems*).—Length: About 6 cm to 7 cm. Strength: Strong. Angle: Mostly upright. Color: Distally, close to N144B and proximally, close to 155A.

*Reproductive organs.*—Androecium: Stamen quantity per flower: About six. Anther size: About 0.5 mm by 0.8 mm. Anther color: Close to 8B to 8C. Pollen amount: None observed.

*Seeds and fruits.*—Seed and fruit development have not been observed on plants of the new *Lomandra* as only male flowers are formed.

Pathogen and pest resistance: Plants of the new *Lomandra* have not been shown to be relatively resistant to root rot, *Phytophthora cinnamomi*. Plants of the new *Lomandra* has not been observed to be resistant to pests or other pathogens common to *Lomandra* plants.

Garden performance: Plants of the new *Lomandra* have been observed to have good garden performance and to tolerate shade, wind, drought, rain and to be hardy to USDA Hardiness Zone 8a.

It is claimed:

1. A new and distinct *Lomandra* plant named 'Sprilomjan' as illustrated and described.

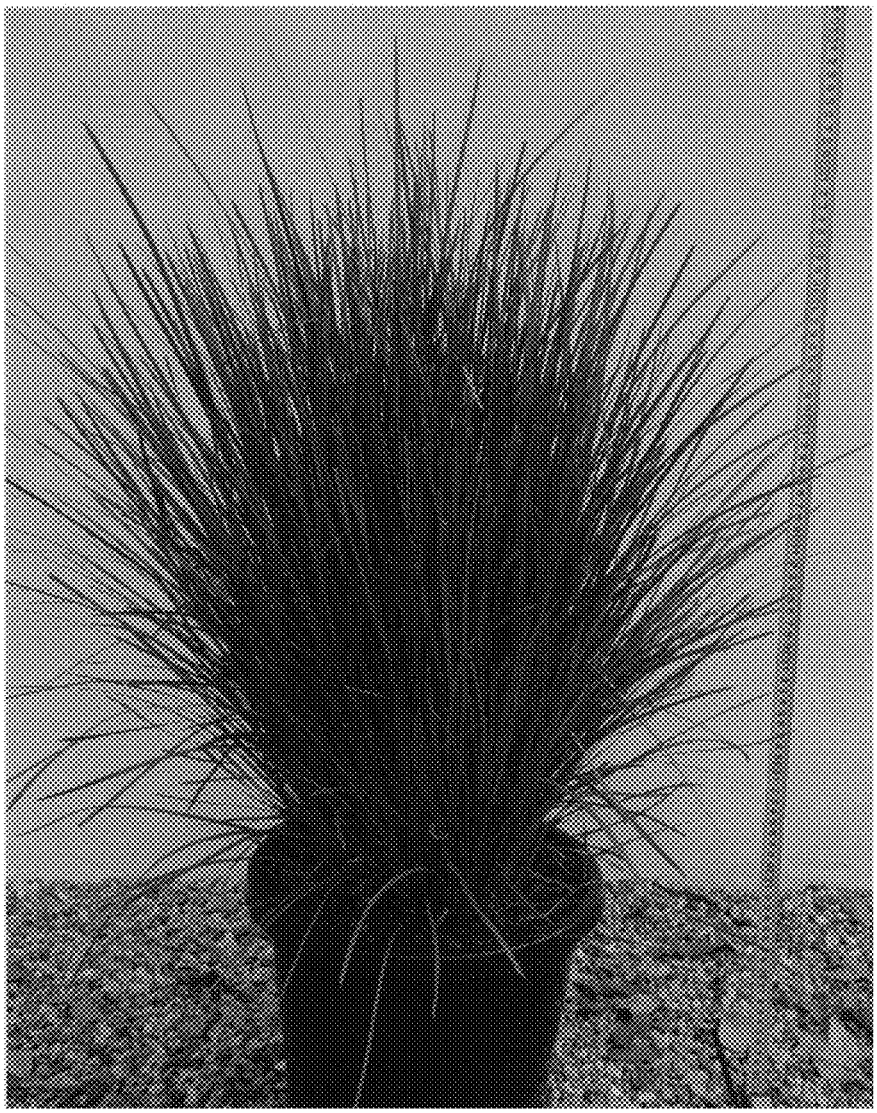

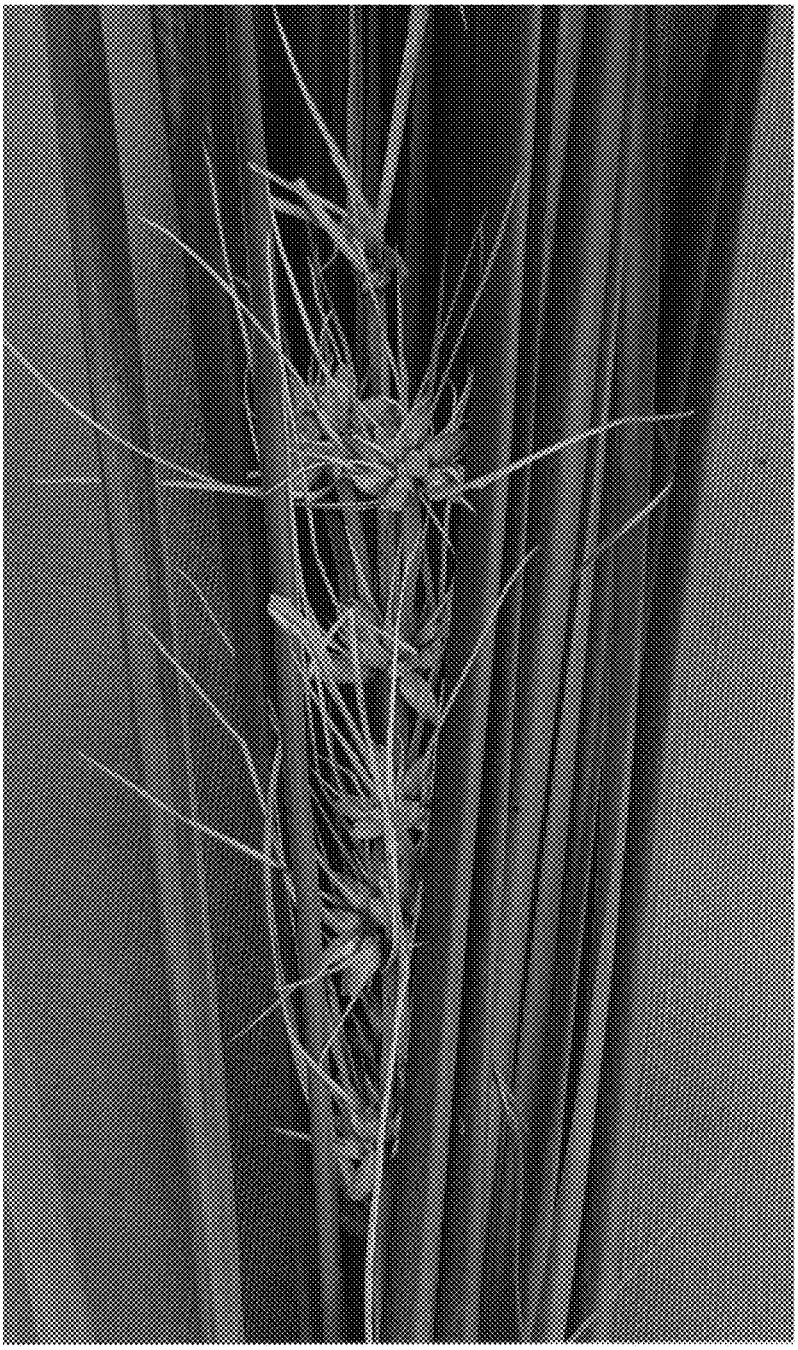

* * * * *